(12) United States Patent
Topaz

(10) Patent No.: US 7,972,617 B1
(45) Date of Patent: Jul. 5, 2011

(54) ANTI-THROMBOGENIC DEVICE AND METHOD OF MANUFACTURING THE SAME

(76) Inventor: Stephen R. Topaz, St. Helens, OR (US)

( * ) Notice: Subject to any disclaimer, the term of this patent is extended or adjusted under 35 U.S.C. 154(b) by 1420 days.

(21) Appl. No.: 11/454,811

(22) Filed: Jun. 15, 2006

(51) Int. Cl.
*A61F 2/02* (2006.01)

(52) U.S. Cl. .................................................. 424/425

(58) Field of Classification Search ................. None
See application file for complete search history.

(56) References Cited

U.S. PATENT DOCUMENTS

| | | | |
|---|---|---|---|
| 3,457,098 A * | 7/1969 | Grode et al. | 428/413 |
| 4,219,520 A | 8/1980 | Kline | |
| 5,441,759 A | 8/1995 | Crouther | |
| 6,261,271 B1 | 7/2001 | Solomon | |
| 6,270,788 B1 | 8/2001 | Koulik | |
| 6,630,460 B2 | 10/2003 | Koulik | |
| 6,774,278 B1 | 8/2004 | Ragheb | |
| 6,790,228 B2 | 9/2004 | Hossainy | |
| 6,830,583 B2 | 12/2004 | Shah | |
| 6,953,625 B2 | 10/2005 | Koulik | |

* cited by examiner

*Primary Examiner* — Carlos Azpuru
(74) *Attorney, Agent, or Firm* — Ingrid McTaggart

(57) ABSTRACT

One embodiment of an anti-thrombogenic device includes a substrate, an attachment compound including a first end directly, mechanically secured to the substrate a second end positioned opposite the substrate, and an anti-thrombogenic species bonded to the second end of the attachment compound.

7 Claims, 1 Drawing Sheet

ANTI-THROMBOGENIC DEVICE AND METHOD OF MANUFACTURING THE SAME

BACKGROUND

Medical devices may be implanted or placed in live beings, such as human patients, for a variety of medical reasons. In many cases the medical device will not function optimally if it does not include anti-thrombogenic, i.e., anti-clotting, properties. Accordingly, a device that includes anti-thrombogenic properties will provide beneficial medical functionality.

DETAILED DESCRIPTION OF THE DRAWINGS

One important property of some medical devices that contact blood after implantation or insertion into a human or animal body is anti-thrombogenicity, i.e., the ability to reduce or eliminate clotting of blood on or at the medical device. For blood to clot, it is believed that thrombin must be generated in the blood. Several anticoagulants are known that are able to prevent the formation of thrombin. The anticoagulant most widely used during surgical procedures is heparin. When heparin is immobilized on the surface of a medical device the ability of clots to form on the surface is reduced or, in other words, the surface becomes anti-thrombogenic. However, many hepranized surfaces degrade over a relatively short time period, meaning that the anti-thrombogenic properties of the surface, and the functionality of the medical device, also degrade rapidly over a short time period. Accordingly, a device and a method of manufacturing the same that provides a securely attached heparin compound may increase the longevity and functionality of the medical device. The device and method of the present invention provides a heparin compound that is mechanically, directly secured to the medical substrate itself thereby providing a medical device with high functionality and longevity.

Figure 1:
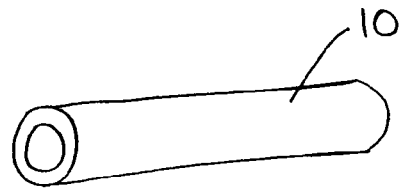
FIG. 1 is a schematic view of one embodiment of an anti-thrombogenic device of the present invention.

Referring to FIG. 1, one example of a method of forming one embodiment of an anti-thrombogenic or anti-coagulant device 10 will be described. In the embodiment shown, device 10 is a section of medical tubing. In other embodiments, device 10 may be any device that may come into contact with blood or blood products, such as catheters, shunts, cannulae, needles, spring guides, and other devices, such as implanted or semi-implanted medical devices, including artificial hearts and components thereof, and devices related to dialysis, to name a few.

Figure 2:
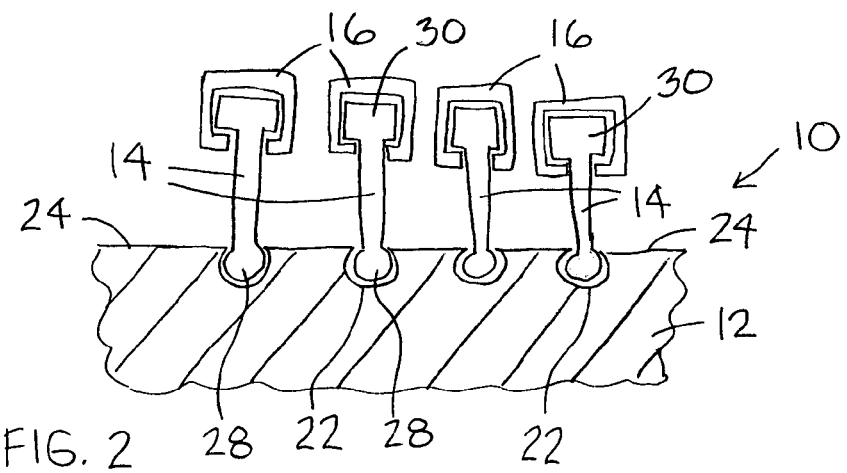
FIG. 2 is a schematic detailed partial cross-sectional view of one embodiment of an anti-thrombogenic device showing an oriented attachment compound mechanically secured to a substrate and an anti-thrombogenic compound attached to the attachment compound.

Referring to FIG. 2, the anti-thrombogenic device 10, shown schematically, may include a substrate 12 with an attachment compound 14 mechanically secured thereto, and an anti-thrombogenic compound 16 attached to the attachment compound. The substrate 12 may be manufactured of any suitable material, for example, plastic such as vinyl, namely, polyvinylchloride (PVC), polycarbonate, and the like.

Figure 3:
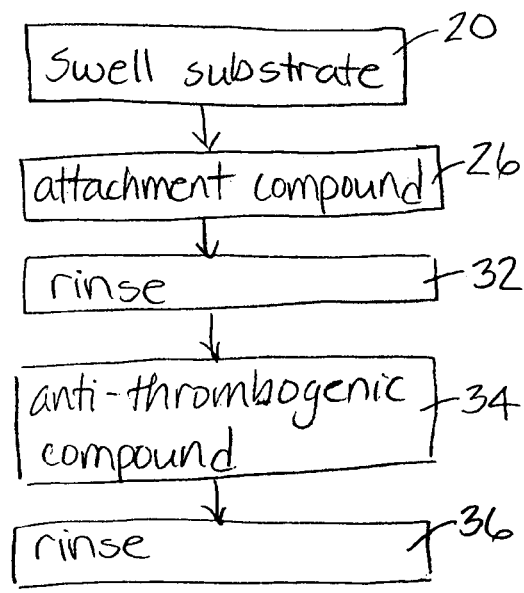
FIG. 3 is a flow chart of one example of a method of manufacturing one embodiment of a device the present invention.

Referring to FIGS. 2 and 3, one example method includes the following steps. As a first step 20, a substrate 12 may be mechanically swelled, i.e., enlarged in size, thereby providing multiple mechanical attachment structure 22, such as openings, at a surface 24 of the substrate 12. In the schematic shown in FIG. 2, openings 22 are shown having a generally round cross sectional shape. However, the size and shape of attachment structure 22 may vary and may be dependent on the swelling agent and substrate utilized in a particular method.

As a second step 26, the substrate 12 may be placed in a solution of an attachment compound 14 such that an end region 28 of the attachment compound 14 (end region 28 is shown schematically in FIG. 2 as a rounded end region sized to be received within round openings 22) may mechanically penetrate into a structural opening 22 of surface 24 of the swelled substrate 12, leaving another end region 30 (shown schematically in FIG. 2 as a square end region) freely exposed. Penetration of an end 28 of attachment compound 14 into attachment structure 22 may be referred to as "dieing" the attachment compound 14 into substrate 12.

In a preferred method, the first and second steps, 20 and 26, may be performed at the same time, i.e., the substrate 12 may be placed into a solution containing both a swelling compound and an attachment compound such that as openings 22 are formed in surface 24, first end region 28 of attachment compound 14 immediately penetrates into and is secured within openings 22 of substrate 12. Such a combination of steps 20 and 26 into a single step may decrease the time of the manufacturing method and may increase the number of openings 22 that receive an attachment compound 14 therein. Accordingly, attachment compound 14 is attached directly and mechanically to substrate 12, such that there is no coating or "priming" layer, such as graphite, coated on top of surface 24, as in prior art methods. In another embodiment, steps 20 and 26 may be conducted sequentially.

As a third step 32, substrate 12 with attachment compound 14 mechanically secured thereto may be rinsed, such as with water, to remove the swelling agent and any unattached attachment compound 14.

As a fourth step 34, the substrate 12, with attachment compound 14 mechanically secured thereto, may be placed in a solution containing an anti-thrombogenic material 16 (shown schematically in FIG. 2 as a hollow box shape sized to be received on the square shaped end region 30 of attachment compound 14). Anti-thrombogenic material 16 may then attach itself to the freely exposed end 30 of the attachment compound 14, thereby attaching itself to the substrate 12. This method will provide a substrate 12 having an anti-thrombogenic compound 16 mechanically secured directly to and into the substrate without the use of a coating on substrate 12. The mechanical securement provided by the method of the present invention is much stronger than the relatively weak bond of an anti-thrombogenic compound attached to a coating which is covalently attached to a substrate, as provided in prior art methods. Such covalent bonding of prior art devices often breaks after a relatively short time period so that the anti-thrombogenic compound is no longer attached to the device, thereby reducing the effectiveness of the medical devices of the prior art.

As a fifth step 36, the device 10, with anti-thrombogenic compound 16 secured thereto, may be rinsed, such as in a water rinse, to remove any unattached anti-thrombogenic compound 16 therefrom.

The steps of the present invention can be carried out by dip coating, spray coating, painting, wiping or any other suitable method. Dip coating may be preferred in that the substrate 12 is generally entirely submersed, thereby ensuring complete coating of the substrate regardless of shape.

The first step 20 of swelling the substrate 12 may be conducted using any swelling agent. In one example embodiment a chlorinated hydrocarbon may be utilized, such as carbon tetrachloride, when the substrate 12 utilized is vinyl. However, any swelling agent may be utilized that results in the creation of mechanical attachment structure 22 on or in surface 24 of substrate 12 which will then facilitate attachment of an attachment compound 14 thereto. The swelling agent may provide an opening 22 as shown, or may provide an outwardly extending mechanical structure for the mechanical attachment of attachment compound 14 to attach thereto. Preferably, the swelling agent utilized will not completely dissolve or otherwise completely deteriorate substrate 12. Other example swelling agents may include chlorobenzene, chloroform, ether, Freon, methyl chloride, methyl ethyl ketone, and xylene, to name a few.

The attachment compound 14 may be any chemical species or compound that mechanically attaches to the swelled substrate. In one example embodiment, the attachment compound 14 is a detergent having a hydrophobic first end region 28 that mechanically penetrates mechanical openings 22 in the swelled substrate 12, and a hydrophilic second end region 30 which is oriented away from the substrate 12 and thereby is freely exposed for the attachment of the anti-thrombogenic compound 16 thereto. Accordingly, in such an embodiment, the method of the present invention may be described as providing an oriented attachment compound 14 for the attachment of the anti-thrombogenic compound 16 thereto. In other words, as shown in the schematic of FIG. 2, multiple attachment compounds 14 are aligned on substrate 12 each with its first end region 28 secured to substrate 12 and each with its second end region 30 positioned away from substrate 12. Example compounds that may be utilized as the attachment compound 14 include ammonium chloride, benzaconium chloride, and any quaternary ammonium species, such as tridodecylmethyl ammonium chloride (TDMAC), to name a few.

The anti-thrombogenic compound 16 may include any anti-thrombogenic species such as heparin, which refers generally to a heterogeneous group of mucopolysaccharides having anti-coagulant properties, any heparin complex including heparin therein, or any other suitable material. In one example embodiment, the fourth step 34 of attaching an anti-thrombogenic compound 16 such as heparin may include dipping the substrate 12, with the attachment compound 14 secured thereto, into a solution of heparin sodium, 10 GMS, dissolved in water.

The anti-thrombogenic device 10 manufactured by the method of the present invention has also been found to have anti-tissue adherence properties, i.e., testing has shown that when implanted, tissue growth has not occurred on or at the device. Additionally, the anti-thrombogenic device 10 manufactured by the method of the present invention has also been found to have anti-bacterial properties, i.e., testing has shown that bacterial growth has not occurred on or directly adjacent to the device 10 when the device 10 has been implanted within a living being.

Other variations and modifications of the concepts described herein may be utilized and fall within the scope of the claims below.

I claim:

1. A method of manufacturing an anti-thrombogenic device, comprising:
    swelling a substrate;
    mechanically attaching an attachment compound directly to said swelled substrate; and
    bonding an anti-thrombogenic species to said attachment compound.

2. The method of claim 1 further comprising, prior to bonding said anti-thrombogenic species, rinsing said substrate with water.

3. The method of claim 1 wherein said substrate is manufactured of a material chosen from one of vinyl and polycarbonate.

4. The method of claim 1 wherein said attachment compound is an oriented molecule including a hydrophobic end mechanically secured to said substrate and a hydrophilic end having said anti-thrombogenic species bonded thereto.

5. The method of claim 1 wherein said swelling produces an opening in a surface of said substrate, and said mechanically attaching comprises physical penetration of an end of said attachment compound into said opening.

6. The method of claim 1 wherein said swelling may be conducted with a swelling agent chosen from one of carbon tetrachloride, chlorobenzene, chloroform, ether, Freon, methyl chloride, methyl ethyl ketone, and xylene.

7. The method of claim 1 wherein said anti-thrombogenic species is a mucopolysaccharide having anti-coagulant properties.

\* \* \* \* \*